United States Patent
Schonenberger

(10) Patent No.: US 8,529,261 B2
(45) Date of Patent: Sep. 10, 2013

(54) DENTAL IMPLANT SYSTEM AND METHOD FOR IMPLANTATION AND CONSTRUCTION OF THE IMPLANT SYSTEM

(75) Inventor: Alwin Schonenberger, Berg (CH)

(73) Assignee: Denta Vision GmbH, Oftringen (CH)

( * ) Notice: Subject to any disclaimer, the term of this patent is extended or adjusted under 35 U.S.C. 154(b) by 0 days.

(21) Appl. No.: 11/711,406

(22) Filed: Feb. 27, 2007

(65) Prior Publication Data
US 2007/0202465 A1 Aug. 30, 2007

Related U.S. Application Data

(63) Continuation of application No. PCT/CH2005/000506, filed on Aug. 30, 2005.

(30) Foreign Application Priority Data

Aug. 31, 2004 (EP) ................................. 04405542

(51) Int. Cl.
*A61C 8/00* (2006.01)
(52) U.S. Cl.
USPC ............................. 433/173; 433/172; 433/174
(58) Field of Classification Search
USPC ........................ 433/172–176, 201.1
See application file for complete search history.

(56) References Cited

U.S. PATENT DOCUMENTS

| | | | | | |
|---|---|---|---|---|---|
| 2,721,387 | A | * | 10/1955 | Ashuckian | 433/173 |
| 5,195,892 | A | * | 3/1993 | Gersberg | 433/174 |
| 5,458,488 | A | * | 10/1995 | Chalifoux | 433/173 |
| 6,431,867 | B1 | * | 8/2002 | Gittelson et al. | 433/173 |
| 6,663,390 | B2 | * | 12/2003 | Riley et al. | 433/173 |
| 6,726,481 | B1 | * | 4/2004 | Zickmann et al. | 433/173 |
| 6,951,461 | B2 | * | 10/2005 | Odrich et al. | 433/173 |
| 7,291,013 | B2 | * | 11/2007 | Aravena et al. | 433/173 |
| 2002/0031748 | A1 | * | 3/2002 | Crudo | 433/173 |
| 2002/0039718 | A1 | * | 4/2002 | Kwan | 433/173 |
| 2003/0031981 | A1 | * | 2/2003 | Holt | 433/173 |

(Continued)

FOREIGN PATENT DOCUMENTS

| FR | 2695823 A | 3/1994 |
|---|---|---|
| WO | WO 2004/002359 A1 | 1/2004 |

OTHER PUBLICATIONS

International Search Report for International Application No. PCT/CH2005/000506 mailed Nov. 17, 2005 (Form PCT/ISA/210).

(Continued)

*Primary Examiner* — Yogesh Patel
(74) *Attorney, Agent, or Firm* — Larson & Anderson, LLC

(57) ABSTRACT

A dental implant system includes a dental implant having a rotationally symmetrical coronal implant region and a supra-structure element that includes an apically extending sleeve portion, which is capable of being placed on the coronal implant region in a freely selectable rotational position. The edge line of the sleeve portion and the circumferential surface of the coronal implant region form together the physiologically relevant micro gap. After implantation and healing-in of the implant, the supra-structure element is placed on to the coronal implant region. An axial length of the sleeve portion and the rotational position of the supra-structure element relative to the implant are selected in such a manner, that the micro gap extending around the implant comes to lie above the natural bone surface by the biological width. Thus, the axial position and the course of the micro gap are adjustable after the healing-in of the implant.

13 Claims, 4 Drawing Sheets

(56) References Cited

U.S. PATENT DOCUMENTS

| | | |
|---|---|---|
| 2003/0031982 A1 | 2/2003 | Abarno |
| 2004/0053194 A1* | 3/2004 | Carroll .......................... 433/172 |
| 2004/0121286 A1* | 6/2004 | Aravena et al. ............... 433/173 |
| 2004/0265781 A1* | 12/2004 | Coatoam ....................... 433/173 |

OTHER PUBLICATIONS

International Preliminary Report on Patentability for International Application No. PCT/CH2005/000506.

* cited by examiner

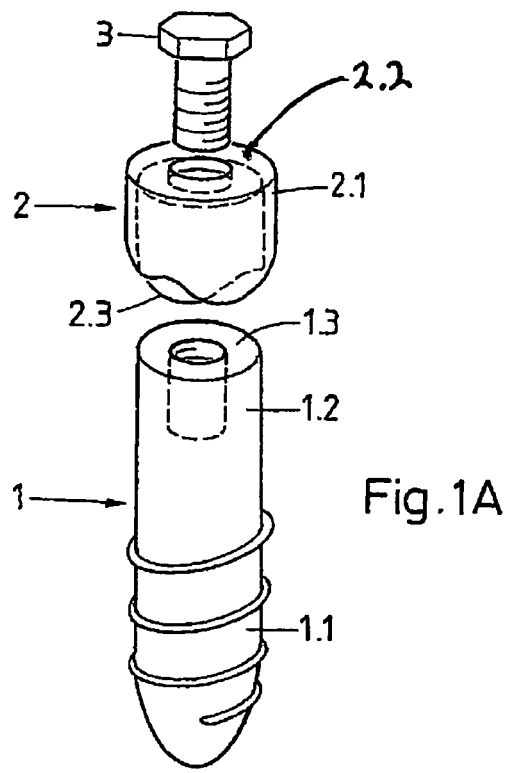
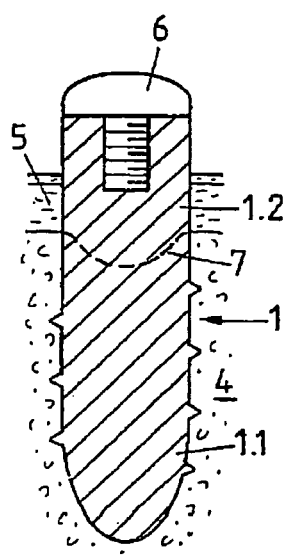
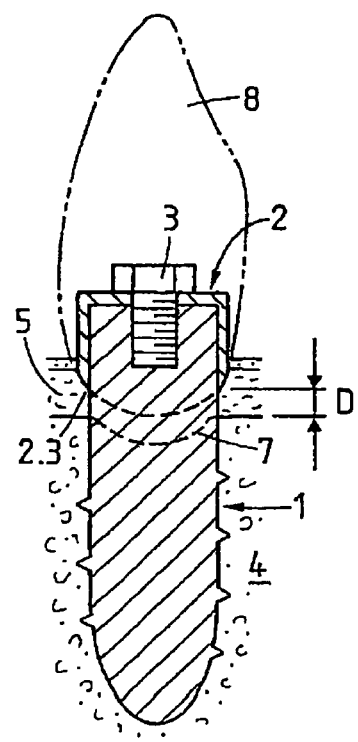
Fig. 1A
Fig. 1B
Fig. 1C

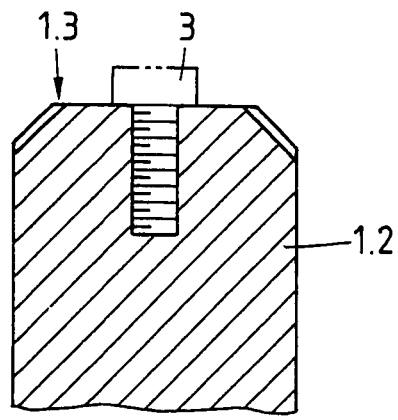
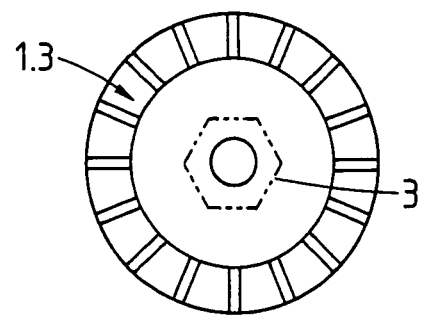
Fig. 7  Fig. 8
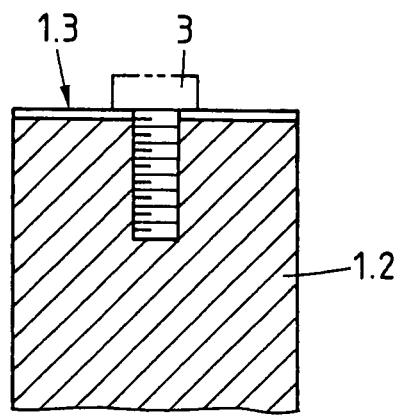
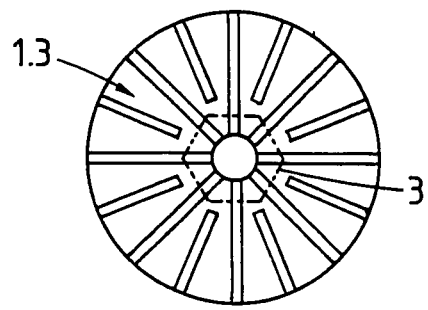
Fig. 9  Fig. 10

DENTAL IMPLANT SYSTEM AND METHOD FOR IMPLANTATION AND CONSTRUCTION OF THE IMPLANT SYSTEM

CROSS-REFERENCE TO RELATED APPLICATIONS

This is a continuation of International Application PCT/CH2005/000506 filed Aug. 30, 2005, which claims priority of European Patent Application No. 04405542.4 filed Aug. 31, 2004, the entire contents of each of which are incorporated herein by reference.

The invention is situated in the field of medical technology and relates to a dental implant system in accordance with the preamble of the first independent claim. The dental implant system comprises a dental implant and at least one supra-structure element, wherein the implant essentially constitutes the root portion of an artificial tooth and the supra-structure element constitutes at least the one part of the crown portion which adjoins the root portion. The invention further relates to a method and a kit in accordance with the preambles of the corresponding, independent claims, wherein the method serves for implantation and build-up of the implant system and the kit is suitable for carrying out the method.

In the dental market different implant systems are available. They are based, for example, on a screw body, on to which an artificial crown or cap is mounted either directly or with an intermediate piece (abutment). For fixing the crown or cap or the abutment, the screw body, for example, comprises an internal thread extending in axial direction from the coronal face. For building up the artificial tooth, an occlusal screw is screwed into this internal thread.

The screw body, for example, is implanted in a corresponding opening in the alveolar bone and for a "covered" healing-in is covered with soft tissue. Following the healing-in, the soft tissue above the implant is removed and the implant is built-up, wherein the separation line between the coronal face of the implant and the supra-structure element (abutment or crown), the so-called micro gap, which extends around the circumference of the built-up implant, comes to lie approximately in the region of the natural bone surface.

Known implants comprise a micro gap, which is predetermined by a coronal face or shoulder of the implant and which in most instances extends in a plane which is perpendicular to the implant axis. It is known, that the micro gap is a physiologically relevant characteristic of a dental implant, because, when an artificial tooth based on an implant is loaded in a natural manner, the bone tissue around the implant develops in such a manner (regression or growth), that the micro gap, like the enamel/cement borderline of a natural tooth, comes to lie on average 2 to 3 mm (biological width) above the bone surface. If therefore the micro gap immediately after the implantation is closer to the bone surface or even inside the bone tissue, the bone will recede. If the micro gap is situated further away from the bone surface, the bone tissue will grow towards the coronal end of the implant, if corresponding conditions prevail and the implant has a surface which promotes bone growth. If the micro gap on the implant is located in a plane perpendicular to the implant axis, the bone tissue will adjust itself in such a manner, that the its surface around the implant essentially also extends in a plane, wherein the plane of the bone surface is situated closer to the apex of the implant than the plane of the micro gap and the distance between the two planes corresponds to the biological width.

On a natural tooth neither the enamel/cement borderline nor the bone surface around the tooth are plane but they are festoon-shaped, i.e. between two teeth they are situated further coronally and lingually/bucally they are situated more apical. When utilising implant systems with the mentioned "plane" micro gaps situated correspondingly close to the bone surface, this festoon-shape is lost due to bone regression, a phenomenon, which is particularly distinctive, when two or more implants are located immediately adjacent to one another.

In order to avoid the above mentioned, undesirable effect of plane micro gaps, implant systems with a predefined festoon-shaped micro gap have been developed. Implant systems of this type are described, for example, in the publication US-2004/0033470 A1 (Wohrle et al.). The implant consisting, for example, of titanium comprises a screw body having a thread and a surface suitable for promoting osseo-integration, and a collar adjoining the coronal end of the screw body and having a coronal face. This coronal face is not plane, but in adaptation to the shape of a natural jaw-bone crest has a curved shape i.e., a festoon-shaped external edge, which predefines the micro gap. It is further proposed to provide a region of the circumferential surface adjacent to the coronal face and having a width approximately corresponding to the biological width with a polished finish (not promoting osseo-integration), wherein the borderline between the osseo-integrative surface (root region) and the polished surface (collar region) is approximately parallel to the external edge of the coronal face, i.e. also festoon-shaped. On this implant an abutment is mounted, by means of an internal thread and a corresponding screw, wherein the face of the abutment which faces towards the implant is adapted to the coronal face of the implant collar, i.e. has a curved shape also.

The micro gap between the implant and the abutment according to US-2004/0033470 does not extend in a plane transverse to the implant axis, but has a festoon shape and is therefore significantly better adapted to the natural shape of the crest of the jawbone. If the implant can be implanted in such a manner, that the festoon-shaped micro gap comes to lie above the natural bone surface by the biological width, it is possible to prevent relevant bone regression. This is not only desirable with respect to the stability of the implant, but also for aesthetic reasons. If, however, the implant is a screw and is to be anchored in the bone tissue by screwing it in, as is described in US-2004/0033470, then the mentioned prevention of bone regression asks for an implantation precision which can hardly be achieved. For the micro gap to be positioned by the biological width above the bone surface and for the festoon-shape of the micro gap to be aligned precisely to the corresponding shape of the natural bone surface, the implant has to be positioned in the bone very precisely not only with respect to depth, but also with respect to its rotational position. For this purpose, it is necessary to match the anchoring depth very accurately to the thread pitch, which is not only difficult to achieve, but in particular in the case of using a thread with a relatively large pitch can be a relevant limitation.

In all the implant systems briefly described above, the axial position and the shape of the micro gap is defined solely by the implant. When the implant is implanted and healed-in and the micro gap, regarding axial position and shape, has not a distance from the bone surface which corresponds to the biological width, it is in most instances not possible anymore to prevent an undesirable change of the bone surface.

It is the object of the invention to eliminate this disadvantage of the known implant systems and to create a dental implant system, with which it becomes possible to adapt the axial position of the micro gap and if so required also its shape to the natural level of the alveolar bone and its shape around the implant or to other circumstances with a precision and simplicity, which cannot be achieved with the known implant systems.

This object is achieved by the dental implant system as defined in the claims.

The fundamental idea of the implant system in accordance with the invention is to have the axial position of the micro gap and possibly also its shape not to be determined by the implant, but by a supra-structure element, which after the implantation and advantageously after the healing-in of the implant is mounted on the implant. Depending on the depth of the implanted implant relative to the bone surface and depending on the shape of the existing or desired bone surface around the implanted implant, a corresponding supra-structure element is selected and/or correspondingly machined in such a manner, that the micro gap will be situated by precisely the biological width above the existing or desired bone surface. This signifies, that with the implant system according to the invention it becomes possible to adjust the micro gap with respect to axial position and shape very precisely to the bone characteristics and that nonetheless much lower demands have to be made of the implantation accuracy than is the case with the known implant systems.

The implant system in accordance with the invention comprises, like known implant systems, a dental implant and at least one supra-structure element. The dental implant has an apical and a coronal implant region. The coronal implant region, for example, adjoins the apical implant region essentially steplessly and has the shape of a cylinder or of a steep truncated cone tapering in coronal direction with, for example, an axial length of approx. 4 to 8 mm. The cylinder or truncated cone of the coronal implant region advantageously comprises a high rotational symmetry relative to the implant axis. Both the apical as well as the coronal implant region comprise an osseo-integratively equipped circumferential surface. The implant advantageously is dimensioned and implanted in a manner suitable for a transmucosal healing-in, i.e. after implantation, its coronal face, which is equipped for the attachment of the at least one supra-structure element, is situated outside of the bone and the mucosal tissue.

The at least one supra-structure element of the implant system according to the invention is cap-shaped and is put over the coronal implant region. When the cap-shaped supra-structure element has been placed upon the coronal implant region, an apically extending sleeve portion of the supra-structure element at least partially surrounds the coronal implant region, wherein the edge of its sleeve portion together with the circumferential surface of the coronal implant region forms the micro gap. The axial length of the sleeve portion determines the exact position of the micro gap on the implant, the form of the apical edge of the sleeve portion determines the shape of the micro gap, which, for example, is festoon-shaped. Whereas on prior art implant systems it is always the coronal face or a shoulder of the implant which determines the axial position and the shape of the micro gap; according to the invention, the axial position of micro gap is to a great extent independent of this coronal implant face. It can be adjusted to have a position on the circumferential surface of the coronal implant region which position is freely selectable within broad limits. The same applies to its shape. A correspondingly prefabricated supra-structure element with a sleeve portion of a desired axial length and if so required with a sleeve portion edge of the desired shape is selected and placed on the coronal implant region. If the edge is festoon-shaped, it is important, that the coronal implant region comprises the rotational symmetry mentioned above, so that the rotational position of the supra-structure element relative to the implant is adjustable within broad limits.

The cap-shaped supra-structure element, for example, is designed as an intermediate piece (mesio-structure), on which, for forming a prosthetic supra-structure, at least one further supra-structure element is mounted with the aid of cement or a buccal screw or bolt connection. The cap-shaped supra-structure element, however, may also constitute the complete supra-structure.

Advantageously, the coronal face of the implant is equipped in such a manner, that, instead of the cap-shaped supra-structure element of the implant system according to the invention, a supra-structure element, which only extends in coronal direction from the coronal face of the implant, can be mounted thereon. The choice of such a supra-structure element is in particular suitable, when the micro gap is not to lie further apically than the face of the implant.

The design of the apical implant region and the design of a coronal portion of the cap-shaped supra-structure element as a mesio-structure or a prosthetic supra-structure are not subjects of this invention. For these features of the implant system according to the invention, reference is made to per se known methods and designs of dental technology.

Exemplary embodiments of the dental implant system according to the invention are described in detail on the basis of the following Figs., wherein:

FIGS. 1A to 1C show a first, very simple embodiment of the implant system according to the invention and its implantation and build-up;

FIGS. 7 to 10 show the coronal region of two further exemplary embodiments of the implant for the implant system according to the invention (FIGS. 7 and 9: axial sections; FIGS. 8 and 10: viewed from above).

Figure 2A:
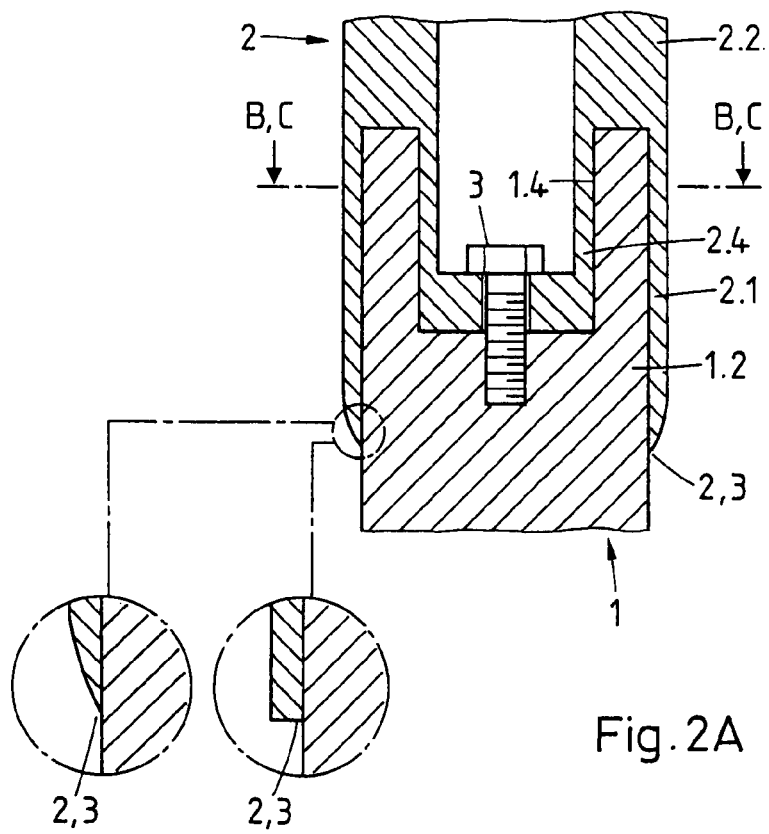
FIGS. 2A to 2C show a preferred embodiment of the implant system according to the invention in an axial section (FIG. 2A) and in a cross section through the coronal implant region and the cap-shaped supra-structure element placed thereon (FIGS. 2B and 2C)

FIGS. 1A to 1C illustrate the main characteristics of the implant system according to the invention and its implantation and build-up on a very simply designed example. As already explained further above and as evident from FIG. 1A, the implant system according to the invention comprises a dental implant 1 and a cap-shaped supra-structure element 2, wherein the implant 1 comprises an apical region 1.1 and a coronal region 1.2 with a coronal face side 1.3 and the supra-structure element 2 comprises a sleeve portion 2.1 extending apically and a face portion 2.2. The coronal implant region 1.2 adjoins the apical implant region 1.1, for example, steplessly and has, e.g. as illustrated, in essence the form of a circular cylinder. The coronal implant region, the same as the apical implant region 1.1, has a surface which is equipped for promoting osseo-integration. The sleeve portion 2.1 of the supra-structure element 2 is adapted to the coronal implant region 1.2 in such a manner, that, when the supra-structure element 2 is placed on the coronal implant region 1.2, the sleeve portion 2.1 of the supra-structure element 2 lies tightly (with the tolerance of approx. 50 µm or less) against the circumferential surface of the coronal implant region 1.2. The face portion 2.2 of the supra-structure element 2 is capable of being attached with suitable means to the coronal face region of the implant 1 (e.g., occlusal screw 3).

It is obvious, that the axial position of the micro gap, which extends between the sleeve portion 2.1 of the supra-structure element and the circumferential surface of the coronal implant region along the edge line 2.3, is dependent on the axial length of the sleeve portion 2.1. The shape of the micro gap is dependent on the course of this edge line 2.3 and the rotational position of this shape is dependent on the relative rotational positions of implant 1 and supra-structure element 2. If the edge line 2.3 is not lying in a plane but has e.g., as illustrated, a festoon-shape, the named relative rotational position is advantageously as freely selectable as possible. This means, that the coronal implant region advantageously comprises a high rotational symmetry, i.e. the implant axis constitutes for the coronal implant region 1.2 a high-pitched rotational axis in such a manner, that this zone is able to be brought into convergence with itself by a rotation around an as small as possible angle. Advantageously, the rotational symmetry is higher than a count of eight (rotation angle for convergence <45°). If the coronal implant region 1.2, as illustrated in FIG. 1, is designed as a circular cylinder and the sleeve portion 2.1 of the supra-structure element 2 is a corresponding hollow cylinder, any relative rotational position of implant 1 and supra-structure element 2 is possible. However, in such a case torsional forces on the built-up tooth have to be transmitted to the implant solely by the attachment means (screw 3), which may not be advantageous. For this reason, it makes sense (see further below) to provide rotationally symmetrical elements between implant 1 and supra-structure element 2 for fixing a selected relative rotational position between implant and supra-structure element.

The implant 1 consists of a material as usually utilised for dental implants, preferably of titanium or of a titanium alloy and its circumferential surface is equipped in a per se known manner for promoting osseo-integration. The apical implant region 1.1 is equipped in a per se known manner for being anchored in the bone tissue, in preference it is designed as a screw, for example, as a self-tapping screw. The cap-shaped supra-structure element 2 consists of a material as usually utilised for artificial teeth, for example of gold, of an alloy with a high gold content, of zirconium or titanium, of a ceramic-metal composite or of a curable plastic material. For attaching the supra-structure element 2 to the coronal face side 1.3 of the implant 1, the implant 1 and the supra-structure element 2, for example, comprise an axial bore, which at least in the implant is equipped with an internal thread, and the supra-structure element 1 is attached to the coronal implant region 1.2 by means of an occlusal screw 3.

FIG. 1B illustrates the implant 1 of FIG. 1A in an implanted condition (axial section). The screw-shaped, apical implant region 1.1 is anchored in the bone tissue 4, the coronal implant region 1.2 extends through the soft tissue 5 and for the healing-in phase, for example, is covered by a healing-in screw 6. The natural bone surface, for example, extends around the implant 1 in a festoon-like manner, as is indicated by line 7.

Following the healing-in phase, which is illustrated by FIG. 1B, the healing-in screw 6 is removed and the supra-structure element 2 is placed upon the coronal implant region 1.2 and attached with the occlusal screw 3, as is illustrated in FIG. 1C. By selecting a supra-structure element 2 having a corresponding axial sleeve length and edge line shape and by selecting a corresponding rotational position of the supra-structure element 2 during the placement as well as, if so required, by a preceding machining of the edge line 2.3, it is possible to adjust the micro gap extending between the circumferential surface of the coronal implant region 1.2 and the sleeve portion 2.1 of the supra-structure element 2, for example, at a position in which it is by precisely the biological width D (usually 2 to 3 mm) above the natural bone surface (line 7). By doing so, bone regression is prevented to a great extent. By adjusting the micro gap or the edge line 2.3 respectively at a lower position, deliberate bone regression to a desired line 7 around the implant 1 is provoked.

The coronal portion of the supra-structure element 2 may be designed as a mesio-structure, i.e. equipped for the placement of a further supra-structure element, e.g., a crown or cap 8. For this purpose, the supra-structure element 2, for example, comprises a coronal portion, on to which the crown or cap 8 can be attached, for example, by means of cement or a lingual screw or bolt connection. It is also possible to utilise the occlusal screw 3 for attaching the further supra-structure element and therefore, for example, to provide the latter with an internal thread in its head zone. A coronal portion of the supra-structure element 2, however, may also be designed as a complete supra-structure, which, for example, by means of an occluso-transversal screw connection is directly attached to the implant 1.

Figure 2B:
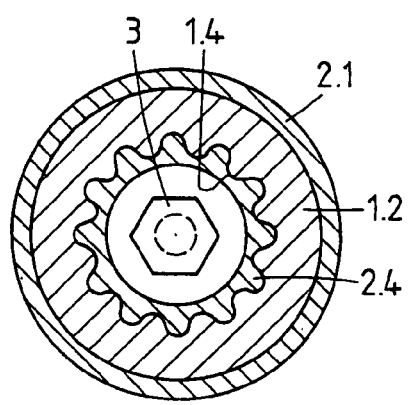
Figure 2C:
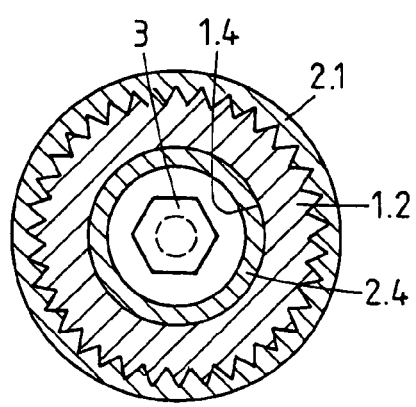

FIGS. 2A to 2C illustrate a preferred embodiment of the implant system according to the invention in an axial section (FIG. 2A) and in a cross section through the coronal implant region 1.2 and the cap-shaped supra-structure element 2 placed thereon (FIGS. 2B and 2C). The same elements are designated with the same reference numbers as in the previous FIGS. The illustrated coronal implant region 1.2 is tube-shaped, i.e. has an axial cavity 1.4. The area of the face portion 2.2 of the supra-structure element 2 is adapted to this cavity 1.4 by carrying an also tube-shaped apical extension 2.4, such that the extension 2.4 is capable of being positioned in the cavity 1.4 and the supra-structure element 2 is capable of being attached to the bottom of the cavity 1.4 by an occlusal screw 3.

The design of the coronal implant region 1.2 with an axial cavity 1.4, in to which the supra-structure element 2 reaches, has the advantage, that force components acting radially on the implant system are absorbed by the intermeshing zones of implant 1 and supra-structure element 2 and therefore do not act on the occlusal screw 3. The latter therefore only has to be dimensioned for the absorption of tensile forces, i.e. may be smaller and in particular thinner than known occlusal screws. Therefore it becomes possible to reduce the implant size compared to sizes of known implants. A further advantage of the countersunk occlusal screw 3 is the fact, that the coronal implant region 1.2 can be machined for a possibly necessary angling (axis correction) of a supra-structure element relative to the implant axis, without the occlusal screw 3 being endangered by such machining.

FIG. 2A illustrates two exemplary embodiments of the edge line 2.3 of the supra-structure element 2. The sleeve portion 2.1 may taper to a sharp edge line or to a rather blunt edge line, so that the edge line forms a step.

FIGS. 2B and 2C illustrate means for fixing the relative rotational positions of implant 1 and supra-structure element 2, which rotational position is selected when the supra-structure element 2 is positioned on the coronal implant region 1.2. According to FIG. 2B, these fixing means are e.g. axially extending, meshing grooves and corresponding ridges arranged on the external surface of the extension 2.4 of the supra-structure element 2 and on the internal surface of the axial cavity 1.4 of the tubular-shaped, coronal implant region 1.2, which both have in essence the form of a round cylinder. For achieving the desired high rotational symmetry, all grooves and ridges are equal and regularly distributed and as many grooves and ridges as possible are provided. According to FIG. 2C, the meshing grooves and ridges are arranged on the essentially cylindrical internal surface of the sleeve portion 2.1 of the supra-structure element 2 and on the also essentially cylindrical circumferential surface of the coronal implant region. Embodiments, in which both inside as well as outside on the tube-shaped, coronal implant region 1.2 and on the corresponding surfaces of the supra-structure element 2 grooves and ridges are provided, are also conceivable.

Implants 1 and supra-structure elements 2 for implant systems according to the invention, as illustrated, for example, in FIGS. 2A to 2C, advantageously are prefabricated in different sizes, i.e., implants with lengths of 10, 12, 14 and 16 mm, all having a same (standardized) coronal implant region. Supra-structure elements adapted to the standardized, coronal implant region are also prefabricated. The prefabricated supra-structure elements comprise sleeve portions of different axial lengths and with e.g. plane edge lines, possibly suitable for later machining. They may also have coronal portions with different angles e.g. of 0°, 10° or 20°. It is also possible, to equip the sleeve portions with edge lines being adapted to the bone course around cutting teeth, canine teeth and side teeth. A suitable implant is implanted and, on the basis of an imprint, which is produced after the healing-in, a supra-structure element is selected and its most favourable rotational position relative to the implant is determined. On the basis of the imprint, it is also determined, how, if so required, the edge line of a prefabricated supra-structure element is to be machined, and if so required, how the coronal implant region is to be machined for an angle correction. It goes without saying, that in every case it is also possible to especially manufacture a supra-structure element 2 on the basis of the imprint.

Figure 3:
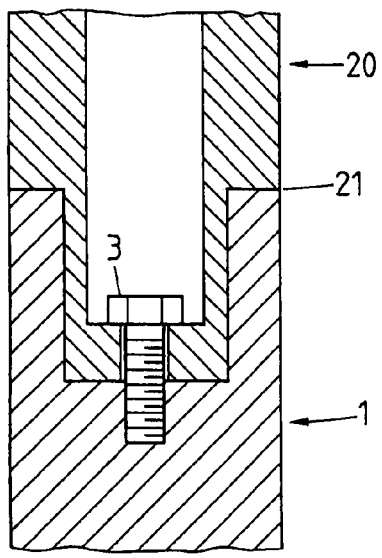
FIG. 3 shows the implant according to the FIGS. 2A to 2C with a supra-structure element extending only coronally from the coronal face of the implant.

FIG. 3 illustrates, that the implant 1 of the implant system according to the invention is also capable of being combined with a supra-structure element 20 which only extends coronally from the coronal face of the implant, i.e. which in comparison with the cap-shaped supra-structure element 2 does not comprise a sleeve portion. In this case the micro gap, as in the case of known implants, is determined by the external edge 21 of the coronal face of the implant and, for example, extends in a plane. The variant according to FIG. 3, however, provides the implant system with a further flexibility. After healing-in of the implant, it is possible to select a cap-shaped supra-structure element or a supra-structure element 20 which extends only coronally, i.e. to decide as to whether the micro gap is to be displaced from the coronal face of the implant in an apical direction or not.

Figure 4:
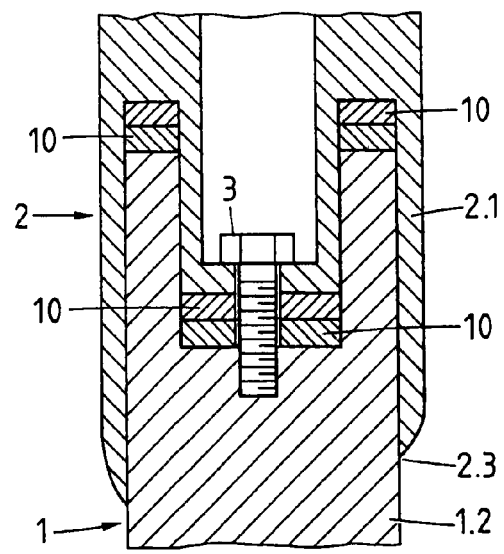
FIGS. 4 to 6 are axial sections through further, exemplary embodiments of the implant system or the implant according to the invention.

FIG. 4 illustrates a further method, with which on a combination of a prefabricated implant 1 and a prefabricated supra-structure element 3 essentially designed as described further above in conjunction with FIGS. 2A to 2C, the axial position of the edge line 2.3 of the supra-structure element 2 can be adjusted on the circumferential surface of the coronal implant region 1.2. For this purpose, spacer rings 10 are inserted on the bottom of the axial cavity 1.4 and/or on the coronal implant face and if so required a correspondingly longer occlusal screw 3 is utilised.

For a displacement of the micro gap in an apical direction it is also possible to shorten the coronal region 1.2 of an implanted implant by corresponding machining (turning to size).

Figure 5:
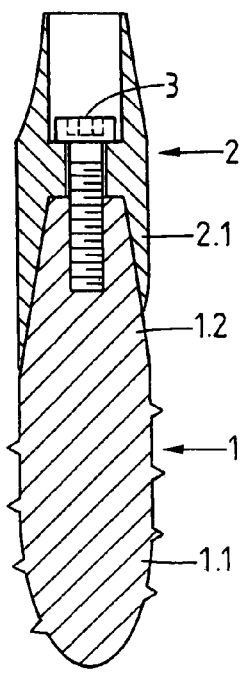

FIG. 5 illustrates a further, exemplary embodiment of the implant system according to the invention, which once again comprises an implant 1 and a cap-shaped supra-structure element 2. In contrast to the embodiments described above, the coronal implant region 1.2 is not designed as a cylinder, but as a truncated cone tapering towards the coronal face (e.g., a circular truncated cone), over which the sleeve portion 2.1 of the supra-structure element 2 is placed in the manner described. The truncated cone advantageously is steep (small angle between circumferential surface and parallels to the implant axis) and in any case directly adjoins the apical implant region 1.1 without a flatter supporting shoulder. Here too, the relative rotational position of implant 1 and supra-structure element 2 or a festoon-shaped edge line 2.3 respectively is freely selectable and if so required capable of being fixed by meshing axial grooves and ridges and the edge line 2.3 can be adapted to natural or desired circumstances by a corresponding machining of the sleeve portion 2.1.

Figure 6:
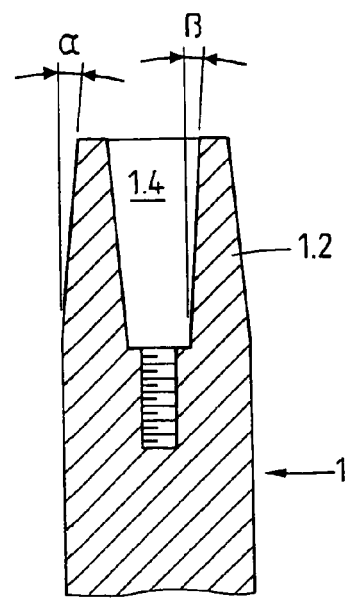

FIG. 6 illustrates a further embodiment of an implant 1 for the implant system according to the invention, which, in essence, is equipped like the implant of FIGS. 2A to 2C or of FIG. 3. In contrast to the implant of the named Figs., the implant according to FIG. 6 has not only a coronal implant region 1.2 which has the form of a steep truncated cone (as in FIG. 5), but also the axial cavity 1.4 has the form of a hollow cone. The steepness of the truncated cone, which forms the coronal implant region 1.2, is determined by the angle $\alpha$ between the circumferential surface and a parallel to the implant axis. This angle $\alpha$ is advantageously no greater than 10°, even more advantageously no greater than 6°. The steepness of the hollow cone (axial cavity 1.4) determined by the corresponding angle $\beta$ may be the same as the steepness of the coronal implant region or less.

FIGS. 7 to 10 illustrate two further embodiments of the coronal implant region 1.2 of a dental implant suitable for the implant system according to the invention. FIGS. 7 and 9 illustrate the coronal implant region 1.2 in an axial section, FIGS. 8 and 10 are views onto the coronal face 1.3.

The difference between the embodiments of FIGS. 7 to 10 and the embodiments described further above lies in the fixing means (e.g., meshing grooves and ridges), with the help of which the relative rotational position between the implant and the supra-structure element is fixed. These means are not arranged on the circumferential surfaces of implant and supra-structure element, but on face sides 1.3 thereof. The illustrated implants do not have an axial cavity on their coronal face side 1.3, but solely a threaded bore for an occlusal screw 3 indicated with a dot-dash line.

In accordance with the FIGS. 7 and 8, the fixing means are arranged on an radially outward area of the face side 1.3 of the coronal implant region 1.2, wherein this area has the form of a truncated cone. It goes without saying, that the face portion of a corresponding supra-structure element (not illustrated) has to be designed in a matching manner. The advantage of the cone-shaped face side 1.3 lies in the fact, that it makes it simpler to shorten the coronal implant region by machining. The fixing means according to FIGS. 9 and 10 extend over the whole, e.g. plane face 1.3 of the coronal implant region.

All grooves and ridges illustrated in FIGS. 7 to 10 extend radially to the axis of the coronal implant region.

The invention claimed is:

1. A dental implant system comprising a dental implant and a hollow supra-structure element, wherein:
 (a) the implant comprises a coronal implant region with a coronal circular face side and with a circumferential surface contiguous with the coronal face side, wherein the coronal implant region is designed as a cylinder and the circumferential surface is equipped for promoting osseo-integration, wherein the coronal implant region comprises a cylindrical cavity;
 (b) the coronal implant region adjoins an apical implant region without a step;

(c) the supra-structure element comprises an upper cylindrical portion with a top circular face, an apical/lower sleeve portion and an extension configured to be inserted into the cylindrical cavity of the implant;

(d) the supra-structure element is configured for attachment to the coronal face side of the implant and the apical/lower sleeve portion is configured to be placed over the coronal implant region in a cap-like manner such that an edge line of the apical/lower sleeve portion lies against the circumferential surface of the implant and forms a microgap, wherein the edge line comprises an inwardly extending curved surface extending towards the upper cylindrical portion and an outwardly extending curved surface extending away from the upper portion; and (e) a position of the edge line is configured to be adjustable by rotating the supra-structure element while the extension is inserted into the cylindrical cavity of the implant.

2. The implant system of claim 1, wherein the edge line is festoon shaped.

3. The implant system of claim 1, wherein the supra-structure and the implant each comprise structures for fixing them in a selected relative rotational position.

4. The implant system of claim 1,
wherein the coronal implant region is tube-shaped and surrounds an axial cavity;
wherein the supra-structure element comprises an extension which is capable of being inserted into the axial cavity; and
wherein the supra-structure element is capable of being attached to the implant in the area of the axial cavity.

5. The implant system of claim 4, wherein the axial cavity has the shape of a hollow cylinder or a hollow cone and is rotationally symmetrical relative to the implant axis.

6. The implant system of claim 4, further comprising means for fixing the rotational position of the supra-structure element relative to the implant disposed on the circumferential surface of the coronal implant region and on the internal surface of the sleeve portion and/or on the internal surface of the axial cavity and the external surface of the extension.

7. The implant system of claim 4, further comprising means for fixing the rotational position of the supra-structure element relative to the implant disposed on a face side of the coronal implant region and on corresponding areas of the supra-structure element.

8. The implant system of claim 1, wherein the supra-structure element and the implant comprise elements for fixing one of many selectable relative rotational positions of implant and supra-structure element after implantation of the dental implant to adjust the relative rotational position of the supra-structure element when the supra-structure element is operatively mounted on the dental implant.

9. The implant system of claim 1, wherein the coronal implant region is configured to have a rotational symmetry.

10. A dental implant kit comprising:
(a) a first dental implant having a coronal implant region and an apical region, wherein
the coronal implant region has a coronal circular face side and a circumferential surface contiguous with the coronal face side, wherein the coronal implant region is designed as a cylinder and wherein the circumferential surface is equipped for promoting osseo-integration, wherein the coronal implant region comprises a cylindrical cavity, and
the coronal implant region adjoins the apical implant region without a step,
(b) a plurality of hollow supra-structure elements suitable for attachment to a coronal face side of the first dental implant, wherein
each of the supra-structure elements comprises an upper cylindrical portion with a top circular face, an apical/lower sleeve portion sized to fit over the coronal implant region of the first dental implant in a cap-like manner, and an extension configured to be inserted into the cylindrical cavity of the implant, wherein each supra-structure element is configured for attachment to the coronal face side of the implant and each apical/lower sleeve portion being configured to be placed over the coronal implant region in a manner such that an edge line of the apical/lower sleeve portion lies against a circumferential surface of the implant and forms a microgap, wherein the edge line comprises an inwardly extending curved surface extending towards the upper cylindrical portion and an outwardly extending curved surface extending away from the upper cylindrical portion, and a position of the edge line is configured to be adjustable by rotating the supra-structure element while the extension is inserted into the cylindrical cavity of the implant, and
the plurality of supra-structure elements comprises subsets of supra-structure elements, wherein the supra-structure elements of one subset are different from the supra-structure elements of other subsets in an axial length.

11. The kit of claim 10, wherein the edge line of each supra-structure element is festoon shaped.

12. The kit of claim 10, wherein the supra-structure elements and the implant each comprise a structure for fixing them in a selected relative rotational position.

13. The kit of claim 10, wherein the kit comprises a plurality of dental implants each having a coronal implant region that is the same as the coronal implant region of the first dental implant.

* * * * *